United States Patent [19]
Pugsley, Jr. et al.

[11] Patent Number: 5,989,268
[45] Date of Patent: Nov. 23, 1999

[54] ENDOSCOPIC HEMOSTATIC CLIPPING DEVICE

[75] Inventors: Charles H. Pugsley, Jr., Pelham, N.H.; Russell F. Durgin, Jr., Attleboro, Mass.

[73] Assignee: Boston Scientific Corporation, Natick, Mass.

[21] Appl. No.: 08/959,727

[22] Filed: Oct. 28, 1997

[51] Int. Cl.$^6$ .................................................. A61B 17/04
[52] U.S. Cl. ........................ 606/144; 606/78; 606/215; 606/216
[58] Field of Search .................................. 606/139, 215, 606/216, 78

[56] References Cited

U.S. PATENT DOCUMENTS

| | | | |
|---|---|---|---|
| 4,665,906 | 5/1987 | Jervis | 128/92 |
| 5,002,563 | 3/1991 | Pyka et al. | 606/222 |
| 5,405,378 | 4/1995 | Strecker | 623/1 |
| 5,417,700 | 5/1995 | Egan | 606/144 |

FOREIGN PATENT DOCUMENTS

WO 96/16603  6/1996  WIPO ............................ A61B 17/04

*Primary Examiner*—Gary Jackson
*Attorney, Agent, or Firm*—Kenyon & Kenyon

[57] ABSTRACT

A medical device for causing the hemostasis of a blood vessel located along the gastrointestinal tract. The medical device comprises a tissue-penetrating device having a pair of hollow jaws, and a clip that is insertable into the tissue-penetrating device. Methods for causing the hemostasis of a blood vessel located along the gastrointestinal tract by using the medical device of the present invention are also provided.

22 Claims, 5 Drawing Sheets

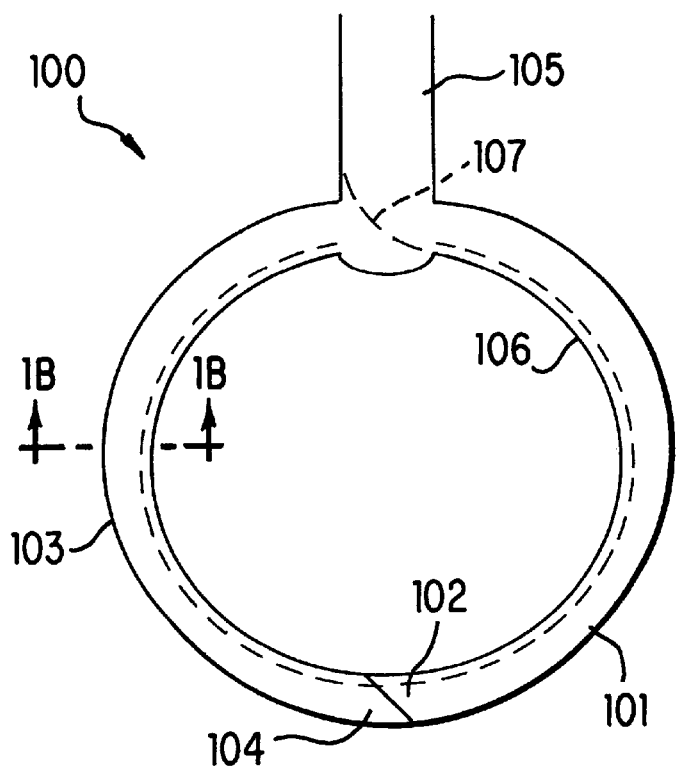
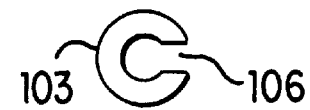
FIG.1B
FIG.1A

ENDOSCOPIC HEMOSTATIC CLIPPING DEVICE

FIELD OF THE INVENTION

The present invention relates to hemostatic clips, and more specifically, to clips which are used to cause hemostasis of blood vessels located along the gastrointestinal tract.

BACKGROUND OF THE INVENTION

Gastrointestinal bleeding is a somewhat common and serious condition that is often fatal if left untreated. This problem has prompted the development of a number of endoscopic therapeutic approaches to achieve hemostasis, such as the injection of sclerosing agents and contact thermo-coagulation techniques. Although such approaches are often effective, bleeding continues for many patients and corrective surgery therefore becomes necessary. Because surgery is an invasive technique that is associated with a high mortality rate and many other undesirable side effects, there exists the need for highly effective, less invasive procedures.

Mechanical hemostatic devices have been used in various parts of the body, including gastrointestinal applications. Such devices are typically in the form of clamps, clips, staples, sutures, etc. which are able to apply sufficient constrictive forces to blood vessels so as to limit or interrupt blood flow. One of the problems associated with conventional hemostatic devices, however, is that they can only be delivered using rigid-shafted instruments via incision or trocar cannula. Moreover, none of the conventional endoscopic hemostatic devices are strong enough to cause permanent hemostasis.

SUMMARY OF THE INVENTION

The present invention provides a medical device for causing the hemostasis of a blood vessel located along the gastrointestinal tract. The medical device includes a tissue-penetrating device comprising a pair of hollow jaws and a clip that is insertable into the tissue-penetrating device. The present invention also includes a method for interluminally causing the hemostasis of a blood vessel located along the gastrointestinal tract by using the medical device.

In one embodiment of the invention, each of the jaws of the tissue-penetrating device is a hollow tubular member having an arc-like configuration and a longitudinal slot. When in a closed configuration, the jaws define an outer diameter. To deploy a clip of the present invention, at least one of the jaws is used to penetrate the gastrointestinal wall. The jaws are then closed and the clip is fed into the tissue-penetrating device such that the clip substantially assumes the shape of the closed jaws. The jaws are then opened such that the clip passes through the longitudinal slot in each of the jaws. The jaws are removed from the tissue, leaving the clip in place.

One advantage of the present invention is that it provides a reliable, definitive treatment for the problem of gastrointestinal bleeding.

Another advantage of the present invention is that it can be delivered via natural body orifices for the control of gastrointestinal bleeding.

Another advantage of the present invention is that it provides a treatment for gastrointestinal bleeding without the need for making a surgical incision.

Yet another advantage of the present invention is that it provides hemostatic clips with sufficient strength to produce permanent hemostasis when deployed.

Another advantage of the present invention is that it provides hemostatic clips which are particularly designed for application to gastrointestinal bleeders.

BRIEF DESCRIPTION OF THE DRAWINGS

FIG. 1 is a cross-sectional view of a tissue-penetrating device, in accordance with the present invention.

DETAILED DESCRIPTION

Figure 2A:
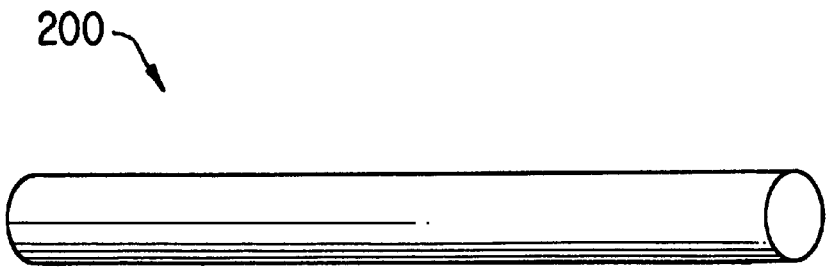
FIGS. 2A and 2B show clip configurations before insertion into a tissue-penetrating device, in accordance with two embodiments of the present invention.

The present invention provides a medical device for causing the hemostasis of a blood vessel located along the gastrointestinal tract. The medical device includes a tissue-penetrating device comprising a pair of hollow jaws and a clip that is insertable into the tissue-penetrating device. The present invention also includes a method for causing the hemostasis of a blood vessel located along the gastrointestinal tract by using the medical device.

In accordance with an embodiment of the present invention, tissue-penetrating device 100 includes a pair of jaws 101 and 103, each terminating at respective distal ends 102 and 104, as shown in FIG. 1. Jaws 101 and 103 are rotatable with respect to each other and are joined by stem 105. Each of jaws 101, 103 and stem 105 are hollow tubular members. The jaws 101, 103 each have a longitudinal slot 106 extending to distal ends 102, 104, respectively. Preferably, at least one of distal ends 102 and 104 is characterized by a sharp tip. Furthermore, distal ends 102 and 104 are preferably interlocking, as shown in FIG. 1. Tissue-penetrating device 100 optionally includes a guiding element 107 for guiding a clip upon insertion into the jaws 101, 103.

Although jaws 101, 103 are shown in FIG. 1 to form a circular configuration when closed, other configurations such as elliptical or irregular, non-symmetric shapes are also within the scope of the invention. In any such configuration, the jaws 101, 103 of tissue-penetrating device 100 preferably define an outer diameter or other dimension of less than 5 mm. Furthermore, it is not necessary that both of jaws 101, 103 be rotatable about stem 105 so long as one of the jaws is moveable with respect to the other to substantially close the jaws.

Tissue-penetrating device 100 is made of any suitable material such as stainless steel or preferably a rigid polymeric material such as high density polyethylene, for example.

Figure 2B:
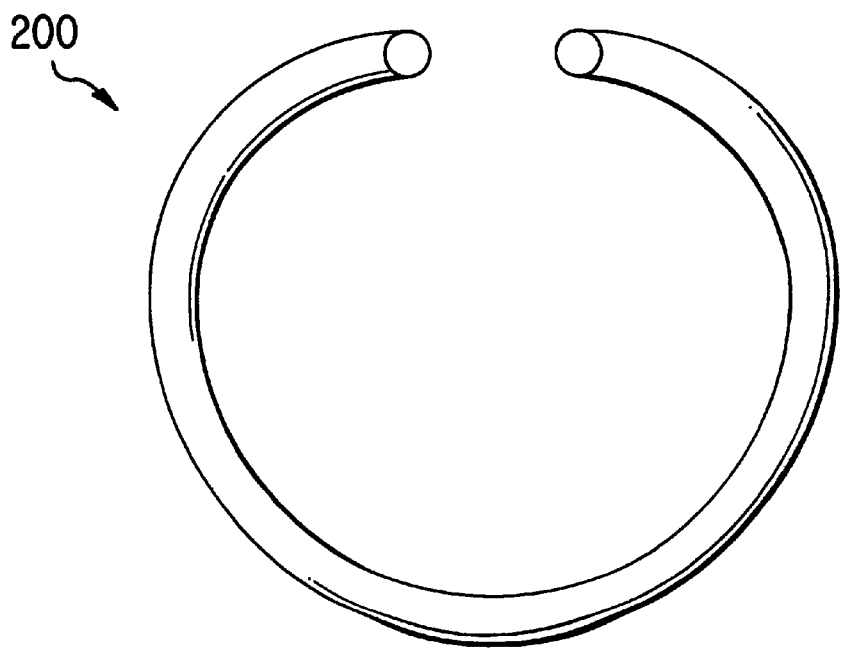

In accordance with the present invention, a hemostatic clip 200 is inserted into tissue-penetrating device 100 through stem 105 and into jaws 101, 103. Prior to inserting clip 200 into tissue-penetrating device 100, clip 200 is generally in a substantially straight configuration as shown in FIG. 2A or preformed to a substantially circular configuration as shown in FIG. 2B. After inserting clip 200 into tissue-penetrating device 100, clip 200 assumes a permanent shape change to substantially the shape of the closed jaws 101, 103 or to any other suitable predetermined configuration.

Clip 200 of the present invention is any suitable material having the strength necessary to produce permanent hemostasis of a blood vessel. By way of example, clip 200 is made from stainless steel or a shape memory alloy such as nitinol. When clip 200 is made from stainless steel, it is preferably a non-elastic stainless steel such that it cannot be appreciably strained without undergoing plastic, non-recoverable deformation. In such a situation, the configuration of clip 200 before being inserted into tissue-penetrating device 100 is virtually any shape, such as either of those shown in FIGS. 2A and 2B. Regardless of the clip configuration, the width of clip 200 is less than the width of longitudinal slot 106 in jaws 101, 103.

Clip 200 can be made from a shape memory alloy, such as nitinol. Shape memory alloys (SMA's) have the ability to "remember" specific shapes which correspond to particular metallurgical phases. If deformed, SMA's can be heated or cooled to invoke a phase transformation, which in turn, causes a transformation in shape. Shape memory alloys are characterized by a transition temperature or transition temperature range, above which the predominant metallurgical phase is termed austenite and below which the predominant phase is termed martensite. The transformation temperatures of SMA's are commonly discussed with reference to $M_s$ and $M_f$, the martensitic start and finish temperatures, respectively, and $A_s$ and $A_f$, the austenitic start and finish temperatures, respectively. The transformation between these phases is reversible such that when alloys are deformed into some first configuration while in the austenitic state, cooled into a martensitic state, deformed into a second configuration, and then re-heated to the austenitic state, the alloy will revert back to the first configuration by virtue of the martensite-to-austenite phase transformation. The use of shape memory alloys in medical devices is known in the art. For example, U.S. Pat. No. 4,485,816, hereby incorporated by reference, discloses the use of a shape memory surgical staple for use in holding the edges of a wound together while it heals. Similarly, U.S. Pat. No. 5,002,563, hereby incorporated by reference, discloses the use of shape memory sutures.

Figure 3A:
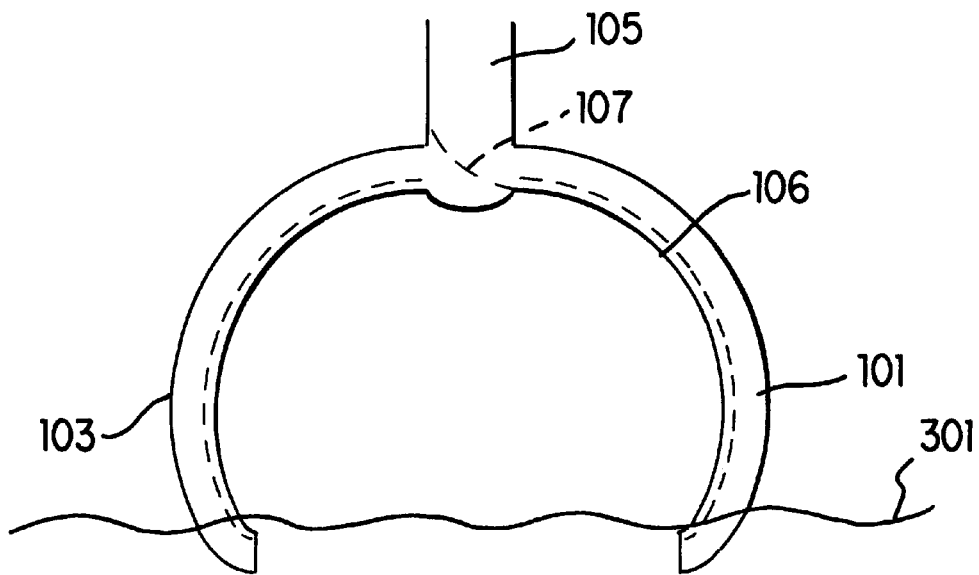
FIGS. 3A–3F illustrate a method of causing the hemostasis of a blood vessel, in accordance with the present invention.
Figure 3B:
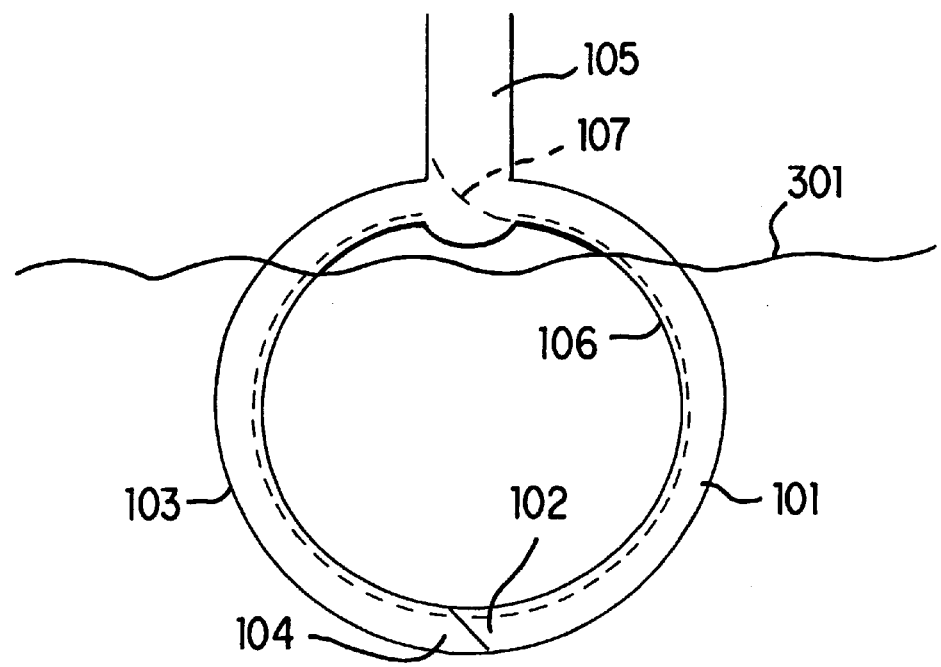
Figure 3C:
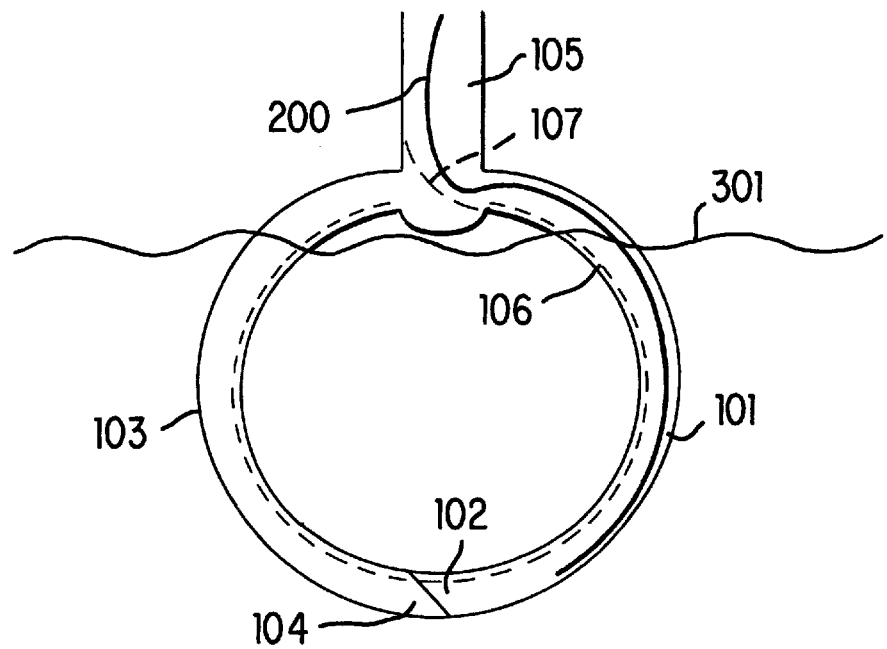
Figure 3D:
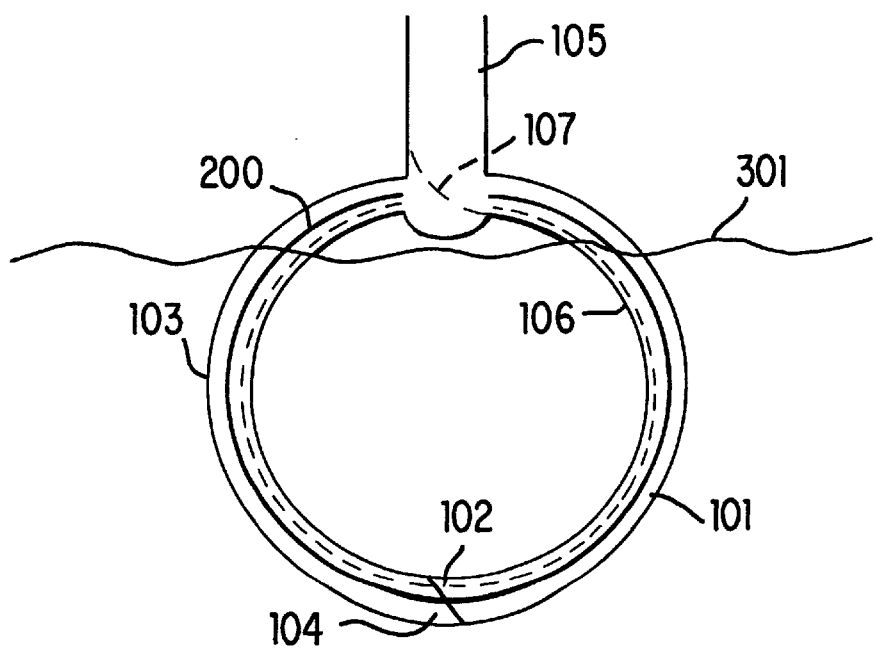
Figure 3E:
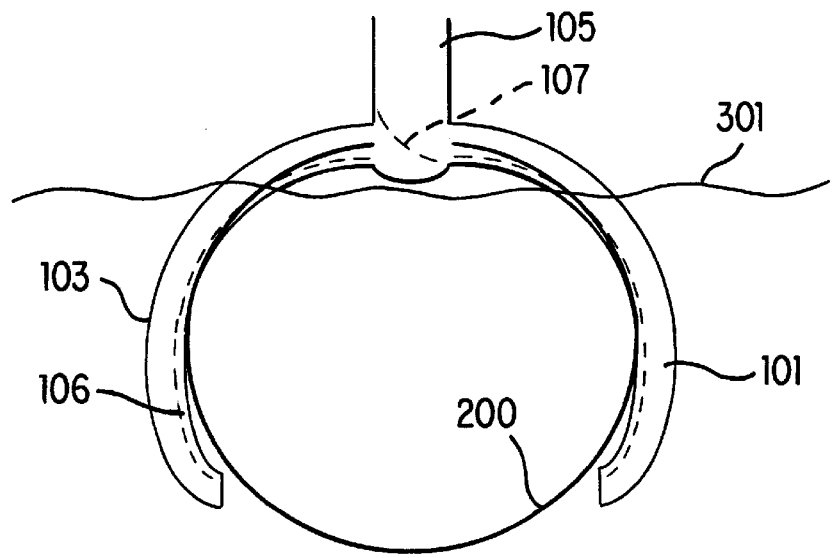
Figure 3F:
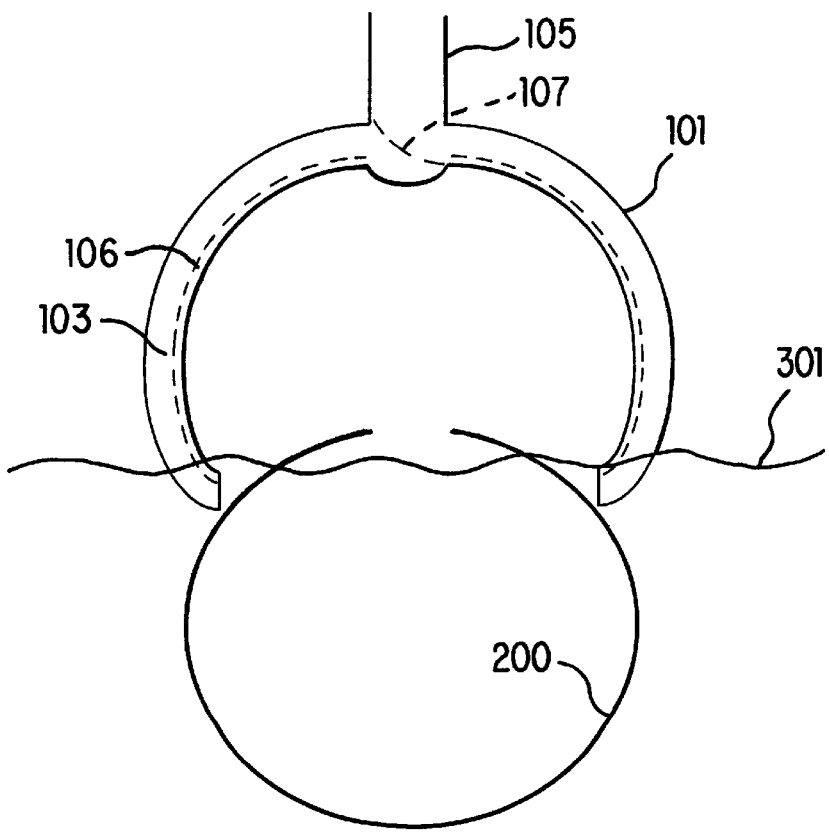

A method used to deploy clip 200 in accordance with an embodiment of the present invention is shown in FIGS. 3A–3F. At least one of the jaws 101, 103 is used to penetrate the gastrointestinal wall 301 as shown in FIG. 3A. The jaws are then closed to form an outer diameter as shown in FIG. 3B and clip 200 is fed into the tissue-penetrating device 100 as shown in FIG. 3C. Optional guiding element 107 directs clip 200 into jaw 101 such that clip 200 substantially assumes the shape of the closed jaws as clip 200 is inserted, as shown in FIG. 3D. The jaws are then opened as shown in FIG. 3E such that the clip passes through the longitudinal slot in each of the jaws. The jaws are removed from the tissue, leaving the clip in place as shown in FIG. 3F.

Tissue-penetrating device 100 is delivered to a target location along the gastrointestinal tract by any known interluminal means. As an example, device 100 is delivered via the working channel of an endoscope or the working channel of an endoscope oversheath. Furthermore, the means by which either or both of jaws 101, 103 are moveable with respect to each other are known in the art.

When clip 200 is made from a non-elastic stainless steel, for example, it is plastically deformed as it is inserted into the jaws 101, 103 of tissue-penetrating device 100. As a result, clip 200 assumes the shape of the inside of the hollow jaws 101, 103. No further treatment of clip 200 is necessary.

When clip 200 is made from a SMA such as nitinol, for example, its austenitic configuration is substantially circular as shown in FIG. 2B. The $A_s$ temperature of the SMA is either less than or greater than body temperature. When clip 200 is made from a SMA having an $A_s$ temperature greater than body temperature, it is cooled such that the SMA is in a martensitic condition prior to insertion into tissue-penetrating device 100. After clip 200 is fully inserted into tissue-penetrating device such as shown in FIG. 3D, it is heated by known means to a temperature above $A_s$, and preferably above $A_f$, to cause a transformation to austenite and the corresponding austenitic configuration. If the pre-set austenitic configuration of clip 200 is substantially circular and has a diameter less than or equal to the outer diameter of jaws 101, 103, the transformation to austenite may not be associated with an appreciable shape change.

When clip 200 is made from a SMA having an $A_s$ temperature less than body temperature, the SMA also has an $M_d$ temperature (i.e., the highest temperature at which martensite can form under stress) greater than body temperature. Such a SMA has the ability to form stress-induced martensite at body temperature. The austenitic configuration of clip 200 is substantially circular, as shown in FIG. 2B. The ability of the SMA to form stress-induced martensite facilitates the insertion of clip 200 into tissue-penetrating device 100. In other words, as clip 200 is inserted into tissue-penetrating device 100 and is thus deformed from its substantially circular austenitic configuration as shown in FIG. 3C, clip 200 at least partially transforms from austenite to stress-induced martensite. As clip 200 continues to be inserted, it eventually arrives at a shape that is substantially similar to its austenitic configuration, as shown in FIG. 3D. Tissue-penetrating device 100 is now removed and clip 200 is in it austenitic state and configuration without the application of heat. Some examples of the use of SMA's having the ability to form stress-induced martensite in medical devices are described in U.S. Pat. No. 4,665,906, incorporated herein by reference.

The present invention provides a medical device and method for the reliable, definitive treatment of gastrointestinal bleeding. Those with skill in the art may recognize various modifications to the embodiments of the invention described and illustrated herein. Such modifications are meant to be covered by the spirit and scope of the appended claims.

What is claimed is:

1. A medical device for causing the hemostasis of a blood vessel located along the gastrointestinal tract, said medical device comprising:

a tissue-penetrating device comprising a pair of hollow jaws; and a clip, said clip being insertable into said tissue-penetrating device, wherein said clip comprises a deformable material that deforms to assume a permanent shape change to substantially the shape of said jaws when said clip is inserted into said tissue-penetrating device.

2. The medical device of claim 1, wherein each of said jaws is a tubular member having a longitudinal slot.

3. The medical device of claim 2, wherein said longitudinal slot is characterized by a width greater than the width of said clip.

4. The medical device of claim 1, wherein at least one of said pair of hollow jaws is characterized by a sharp tip.

5. The medical device of claim 1, wherein said jaws have interlocking distal ends.

6. The medical device of claim 1, wherein said clip is in the form of a wire.

7. The medical device of claim 1, wherein said jaws comprise stainless steel.

8. The medical device of claim 1, wherein said jaws comprise a polymeric material.

9. A method of causing the hemostasis of a blood vessel located along the gastrointestinal tract, said method comprising the steps of:

providing a tissue-penetrating device comprising a pair of hollow jaws, said jaws being rotatable with respect to each other and having an open configuration and a substantially closed configuration, said substantially closed configuration defining an outer diameter;

providing a clip, said clip comprising a deformable material and being insertable into said tissue-penetrating device;

penetrating the gastrointestinal wall with at least one of said jaws when said jaws are in an open configuration;

substantially closing said pair of jaws; and inserting said clip into said tissue-penetrating device, said clip thereby being deformed and assuming a permanent shape change to substantially the shape of said jaws in said substantially closed configuration.

10. The method of claim 9, wherein:

each of said jaws is a tubular member having a longitudinal slot, said longitudinal slot characterized by a width greater than the width of said clip.

11. The method of claim 10, further comprising the step of:

opening said pair of jaws such that said clip passes through said longitudinal slot in each of said jaws.

12. The method of claim 9, wherein said clip comprises stainless steel.

13. A method of causing the hemostasis of a blood vessel located along the gastrointestinal tract, said method comprising the steps of:

providing a tissue-penetrating device comprising a pair of hollow jaws, said jaws being rotatable with respect to each other and having an open configuration and a substantially closed configuration, said substantially closed configuration defining an outer diameter, wherein each of said jaws is a tubular member having a longitudinal slot and at least one of said jaws is characterized by a substantially arc-like configuration;

providing a clip, said clip being in the form of a wire insertable into said tissue-penetrating device, said clip comprising nitinol having an $A_s$ temperature greater than body temperature, wherein the austenitic configuration of the clip is substantially circular and characterized by an outer diameter less than or equal to the outer diameter formed by said pair of jaws when in a substantially closed configuration;

penetrating the gastrointestinal wall with at least one of said jaws when said jaws are in an open configuration;

substantially closing said pair of jaws;

inserting said clip into said tissue-penetrating device, said clip thereby substantially assuming the shape of the jaws when said jaws are in a substantially closed configuration;

opening said pair of jaws such that said clip passes through said longitudinal slot in each of said jaws; and heating the clip to a temperature greater than the $A_s$ temperature of the nitinol.

14. A medical device for causing the hemostasis of a blood vessel located along the gastrointestinal tract, said medical device comprising:

a tissue-penetrating device comprising a pair of hollow jaws; and a clip, said clip being insertable into said tissue-penetrating device, wherein said clip comprises a shape memory alloy.

15. The medical device of claim 14, wherein said shape memory alloy has an $A_s$ temperature less than body temperature and an $M_d$ temperature greater than body temperature.

16. The medical device of claim 15, wherein the austenitic configuration of said shape memory alloy is substantially circular.

17. The medical device of claim 14, wherein the austenitic alloy has an $A_s$ temperature greater than body temperature.

18. The medical device of claim 17, wherein the austenitic configuration of said shape memory alloy is substantially circular.

19. A method of causing the hemostasis of a blood vessel located along the gastrointestinal tract, said method comprising the steps of:

providing a tissue-penetrating device comprising a pair of hollow jaws, said jaws being rotatable with respect to each other and having an open configuration and a substantially closed configuration, said substantially closed configuration defining an outer diameter;

providing a clip, said clip comprising a shape memory alloy and being insertable into said tissue-penetrating device;

penetrating the gastrointestinal wall with at least one of said jaws when said jaws are in an open configuration;

substantially closing said pair of jaws; and inserting said clip into said tissue-penetrating device, said clip thereby substantially assuming the shape of said jaws in said substantially closed configuration.

20. The method of claim 19, wherein said shape memory alloy has an $A_s$ temperature greater than body temperature, and wherein the austenitic configuration of the clip is substantially circular and characterized by an outer diameter less than or equal to the outer diameter formed by said pair of jaws in said substantially closed configuration.

21. The method of claim 20, further comprising heating the clip to a temperature greater than the $A_s$ temperature of the shape memory alloy.

22. The method of claim 19, wherein said shape memory alloy has an $A_s$ temperature less than body temperature and an $M_d$ temperature greater than body temperature, and wherein the austenitic configuration of the clip is substantially circular and characterized by an outer diameter less than or equal to the outer diameter formed by said pair of jaws.

* * * * *